United States Patent [19]

DeLuca et al.

[11] 4,264,513

[45] Apr. 28, 1981

[54] 1α-HYDROXY-25-KETO-27-NOR-CHOLECALCIFEROL AND PROCESSES FOR PREPARING SAME

[75] Inventors: Hector F. DeLuca; Heinrich K. Schnoes, both of Madison, Wis.; Joseph L. Napoli, Jr., Dallas, Tex.; Mary A. Fivizzani, Madison, Wis.

[73] Assignee: Wisconsin Alumni Research Foundation, Madison, Wis.

[21] Appl. No.: 41,081

[22] Filed: May 21, 1979

[51] Int. Cl.$^3$ .................................................. C07J 9/00
[52] U.S. Cl. ........................ 260/397.2; 260/239.55 R; 260/239.55 C
[58] Field of Search ..................................... 260/397.2

[56] References Cited

U.S. PATENT DOCUMENTS

| | | | |
|---|---|---|---|
| 3,993,675 | 12/1976 | Uskokovic et al. | 260/397.2 |
| 4,105,660 | 8/1978 | Jones | 260/397.2 |
| 4,145,346 | 3/1979 | Jones et al. | 260/397.2 |

*Primary Examiner*—Elbert L. Roberts
*Attorney, Agent, or Firm*—Howard W. Bremer

[57] ABSTRACT

The invention provides new vitamin D derivatives as well as new intermediate compounds derived during the processes for preparing such new derivatives. The new derivatives have been identified as 1α-hydroxy-25-keto-27-nor-vitamin $D_3$ and its acylates.

1α-hydroxy-25-keto-27-nor-vitamin $D_3$ expresses excellent vitamin D-like activity and would find ready application as a substitute for vitamin D compounds in the treatment of disease states evincing calcium-phosphorous imbalance.

8 Claims, No Drawings

1α-HYDROXY-25-KETO-27-NOR-CHOLECALCIFEROL AND PROCESSES FOR PREPARING SAME

The invention described herein was made in the course of work under a grant or award from the Department of Health, Education, and Welfare.

DESCRIPTION

Technical Field

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective vitamin $D_3$ must be converted in vivo to its hydroxylated forms. For example, the vitamin is first hydroxylated in the liver to form 25-hydroxyvitamin $D_3$ and is further hydroxylated in the kidney to produce 1α, 25-dihydroxyvitamin $D_3$ or 24,25-dihydroxyvitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

BACKGROUND ART

References to various of vitamin D derivatives are extant in the patent and other literature. See, for example, U.S. Pat. Nos.: 3,565,924 directed to 25-hydroxycholecalciferol; 3,697,559 directed to 1,25-dihydroxycholecalciferol; 3,741,996 directed to 1α-hydroxycholecalciferol; 3,907,843 directed to 1α-hydroxyergocalciferol; 3,715,374 directed to 24,25-dihydroxycholecalciferol; 3,739,991 directed to 25,26-dihydroxycholecalciferol; 3,786,062 directed to 22-dehydro-25-hydroxycholecalciferol; 3,847,955 directed to 1,24,25-trihydroxycholecalciferol; 3,906,014 directed to 3-deoxy-1α-hydroxycholecalciferol; 3,069,321 directed to the preparation of various side chain fluorinated vitamin $D_3$ derivatives and side chain fluorinated dihydrotrachysterol$_3$ analogs.

DISCLOSURE OF INVENTION

A new derivative of vitamin $D_3$ has now been found which expresses excellent vitamin D-like activity and which, therefore, could serve as a substitute for vitamin $D_3$ in its various known applications and would be useful in the treatment of various diseases such as osteomalacia, osteodystrophy and hypoparathyroidism.

This derivative is 1α-hydroxy-25-oxo-27-nor-cholecalciferol (1α-hydroxy-25-keto-27-nor-vitamin $D_3$).

BEST MODE OF CARRYING OUT THE INVENTION

The compound of this invention was synthesized by the process shown in abbreviated form in the following schematic:

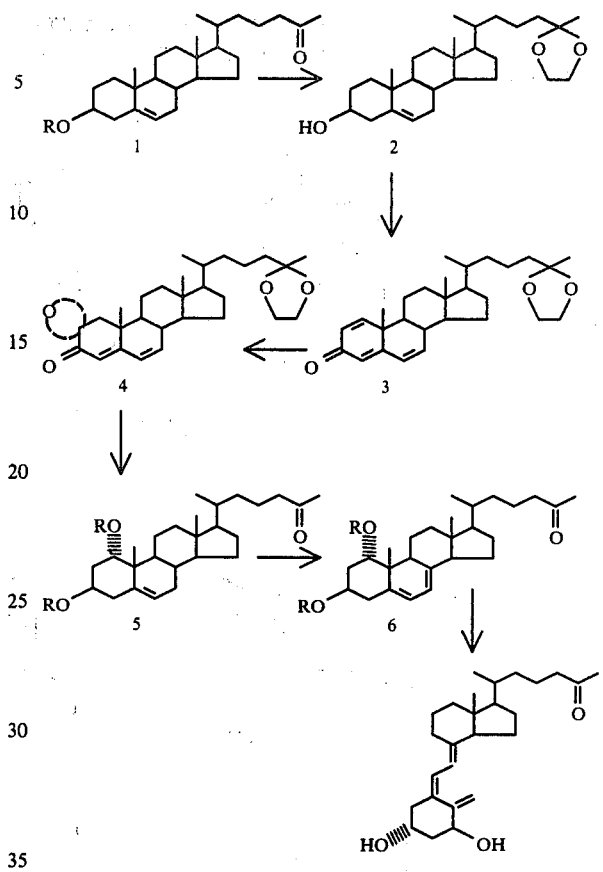

The process involves the conversion of 27-nor-cholest-5-en-25-one (Structure 1, R=H) to the corresponding 25-ketal derivative (2). A 3-acyl derivative of 27-nor-cholest-5-en-25-one (e.g. Structure 1 with R=acetyl or benzoyl) is also a suitable starting material for this reaction step, the acyl group being removed by hydrolysis in base after formation of the 25-ketal. Ketal 2 is subjected to dehydrogenation to yield trienone 3 which is epoxidized with $H_2O_2$ in base to give the 1α,-2α-epoxy-4,6-dien-3-one derivative 4. Reduction of the latter in metal/ammonia solutions (Barton et al, J. Am. Chem. Soc. 95, 2748 (1973)) gives 25,25-ethylenedioxy-27-nor-cholest-5-en-1α,3β-diol from which the ketal protecting group is removed by hydrolysis under acid conditions to yield 27-nor-5-cholesten-1α,3β-diol-25-one (compound 5, with R=H). Subsequent acylation of this intermediate (acetylation, benzoylation, etc.) gives the 1,3-diacyl derivative (compound 5, where R=acyl) which is converted to the 5,7-diene derivative (6, R=acyl) by several known processes, e.g. the method of Hunziker and Müllner (Helv. Chim. Acta 61, 70 (1958) or via the 7-keto and 7-tosylhydrazone intermediates (Onisko et al, Bioorganic Chem. 6, 203 (1977). If desired the acyl groups can be removed at this stage by mild base hydrolysis (e.g. 10% alcoholic KOH) to yield the corresponding 1,3-dihydroxy derivative. Ultraviolet irradiation of a solution of the 5,7-diene 6(R=acyl) yields the 27-nor-25-keto-1α-hydroxy-previtamin $D_3$ diacylate, which is isomerized to the corresponding vitamin $D_3$ analog by heating, and after removal of the acyl groups by mild basic hydrolysis, yields the desired 27-nor-25-keto-1α-hydroxyvitamin D₃ (compound 7).

An alternative preparative route to 1α-hydroxy-25-keto-vitamin analog 7 is illustrated by the process schematic below.

hydroxy-cyclovitamin derivative (10) using the procedures of Paaren et al (Proc. Nat. Acad. Sci. 75, 2080 (1978)). Direct solvolysis of 10 yields, after purification, the 1α-hydroxy-3-O-acyl product 11 (where the acyl group, R, corresponds to the acyl moiety of the organic

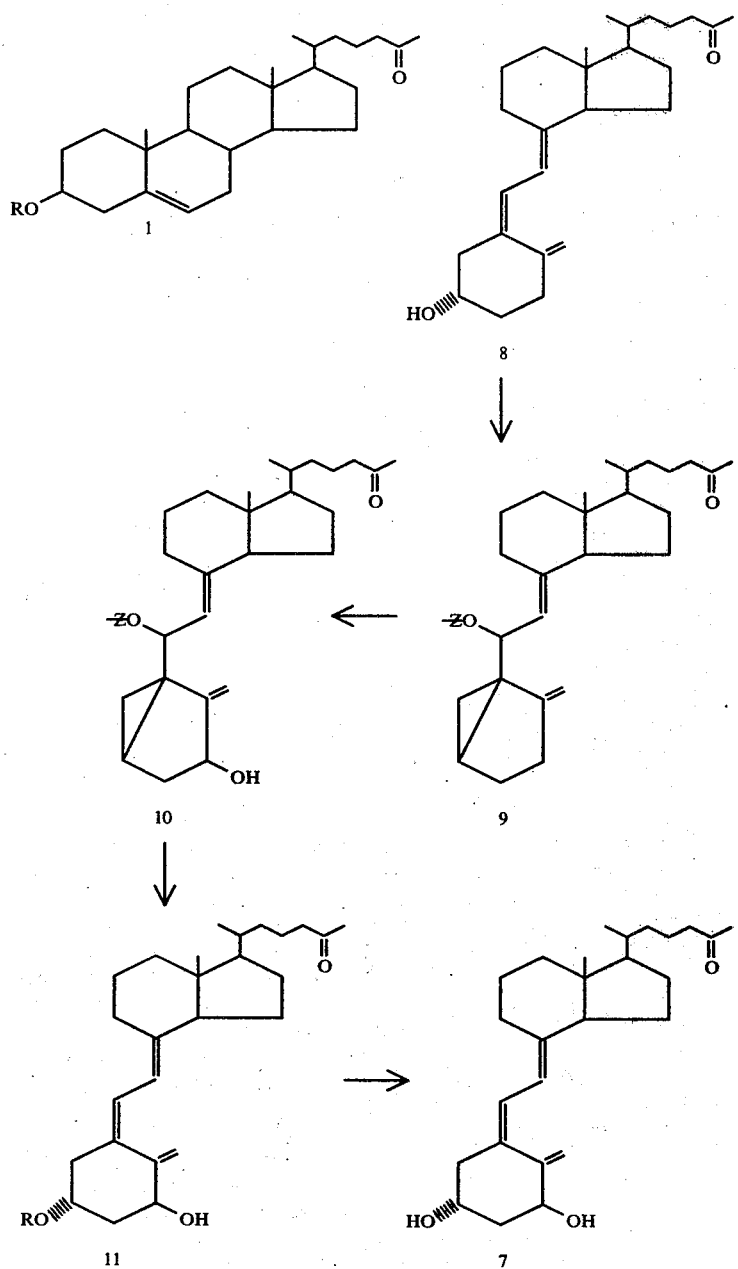

This process involves the conversion of the same starting material (compound 1, where R is acyl, e.g. acetyl or benzoyl) to the known 27-nor-25-ketovitamin D₃ product (compound 8) using for example the procedures of Blunt and DeLuca (Biochemistry, 8 671 (1969)). This vitamin analog is converted to its 3-tosyl derivative which is solvolyzed to the 3,5-cyclovitamin derivative (9) where Z corresponds to the alkyl portion of the alcoholic solvent used in solvolysis, i.e. Z is typically methyl or ethyl but can also be hydrogen if solvolysis is conducted in aqueous media). This intermediate, in turn, is oxidized with selenium dioxide to the 1α-carboxylic acid used for solvolysis, i.e. R is typically acetyl of formyl) and this acylated intermediate is then readily hydrolyzed in mild base to 1α-hydroxy-25-keto-27-norvitamin D₃ (compound 7).

In the following examples, the numbers identifying specific products refer to the compounds so numbered in the preceding process schematics.

EXAMPLE 1

25,25-Ethylenedioxy-27-nor-cholest-5-en-3β-ol.

A solution of 3β-hydroxy-27-nor-cholest-5-en-25-one 3-acetate (1, R=acetyl) (1.0 g, 2.33 mmol) and p-toluenesulfonic acid (100 mg) dissolved in dry benzene (150 ml) containing ethylene glycol (18 ml) was distilled slowly over 8.5 hr. Thin layer chromatography (TLC) (20% acetone/hexane) showed one product spot (Rf 0.55) and no remaining starting material. The reaction was cooled and benzene and water were added. The phases were separated and the aqueous phase was extracted with additional benzene. The combined organic phases were washed twice with water and once with brine. The solvent was removed to give 25,25-ethylenedioxy-27-norcholest-5-en-3β-ol 3-acetate: NMR (270 MHz) δ0.67 (s, 18—$CH_3$) 0.93 (d, J=$CH_3$, 21—$CH_3$), 1.01 (s, 19—$CH_3$), 1.28 (s, 26—$CH_3$), 2.03 (acetate—$CH_3$), 2.91 (ethylene ketal), 4.52 (broad m, 3α—H), 5.27 (m, 6—H).

The product was dissolved in ether (5 ml) and 1 M KOH/methanol (4 ml) and allowed to stand at ambient temperature for 2 hr. TLC (20% acetaone/hexane) showed reaction product (Rf 0.23). Ether and water were added and the phases were separated. The aqueous phase was extracted with ether. The combined organic phases were washed twice with water and once with brine, and dried over $K_2CO_3$. The solvent was removed and the residue was recrystallized from ether to give 25,25-ethylenedioxy-27-norcholest-5-en-3β-ol, compound (2) (0.7 g); mp 135°–136° C. A further 270 mg of (2) which showed only one spot on TLC analysis was recovered rrom the mother liquors: NMR (270 MHz) 0.67 (s, 18-$CH_3$), 0.93 (d, J=6.2 $H_3$, 21—$CH_3$), 1.01 (s, 19—$CH_3$), 1.31 (s, 26—$CH_3$), 3.93 (ethylene ketal), 3.52 (broad m, 3α-H), 5.35 (m, 6—H).

EXAMPLE 2

25,25-Ethylenedioxy-27-nor-cholesta-1,4,6-triene-3,25-dione (3).

A mixture of (2) (0.046 g, 0.11 mmol) and 2,3-dichloro-5,6-dicyano-1,4-benzo-quinone (0.08 g, 0.35 mmol) in dioxane (1 ml) were refluxed for 22 hr. The reaction mixture was cooled and filtered. The residue obtained after evaporation of the solvent was filtered through a neutral alumina column (0.5×7 cm) eluted with methylene chloride. The material obtained was chromatographed on a preparative plate developed twice with 15% acetone/hexane to give two products. The product with Rf 0.21 was the desired compound (3) (10 mg); NMR (60 MHz) 0.78 (s, 18—$CH_3$), 0.93 (d, J=6 Hz, 21—$CH_3$), 1.18 (s, 19—$CH_3$, 1.30 (s, 26—$CH_3$), 3.93 (ethylene ketal), 5.90, 6.05, 6.22 (three m, triene protons); 6.98 (d, J=10 Hz, triene protons).

The product with Rf 0.15 was identified as 27-nor-cholest-1,4,6-triene-3,25-dione (9.3 mg); NMR (60 MHz) 0.78 (s, 18—$CH_3$), 0.93 (d, J=6 Hz, 21—$CH_3$), 1.18 (s, 19—$CH_3$), 2.1 (s, 26—$CH_3$), 5.90, 6.03, 6.22, (three multiplets, triene protons), 6.95 (d, J=10 Hz, triene H).

EXAMPLE 3

25,25-Ethylenedioxy-1α,2α-oxido-27-nor-cholest-4,6-diene-3,25-dione (4).

To a solution of 3 (0.14 g, 0.33 mmol), in methanol (5 ml) and benzene (4 ml) was added 10% methanolic NaOH (0.04 ml) and 30% $H_2O_2$ (0.24 ml). After 16 hr at ambient temperature, the reaction mixture was cooled to −5° C. and poured over ice. The material obtained after extraction of the aqueous phase with methylene chloride was chromatographed on a preparative layer developed three times with 30% acetone/hexane to give 0.09 g of the 1α,2α-epoxide 4 (Rf 0.66): UV (hexane) $\lambda_{max}$ 279, 288 nm (shoulder); NMR (60 MHz) δ0.78 (s, 18—$CH_3$), 0.93 (d, J=5 Hz, 21 $CH_3$), 1.14 (s, 19—$CH_3$), 1.25 (s, 26—$CH_3$), 3.87 (ethylene ketal), 3.35 (dd, J=4.5 Hz, 2 Hz, epoxy H), 3.52 (d, J=4.5 Hz, epoxy H), 5.54 (d, J=1.8 Hz), 5.97 (s).

EXAMPLE 4

1α,3β-Dihydroxy-27-norcholest-5-en-25-one 1,3-diacetate (5, R=acetyl).

To a solution of Na (0.1 g) in distilled liquid $NH_3$ (7 ml) at −33° C. was added in one portion compound 4 (0.09 g, 0.2 mmole) in THF (7 ml). After 5 min, $NH_4Cl$ (0.7 g) was added in small portions over 0.75 hr. The $NH_3$ was evaporated and replaced with ether. The ether phase was washed with water, 1 N HCl, water, brine, and dried ($Na_2SO_4$). The residue obtained after evaporation of the ether was chromatographed on a preparative-layer developed twice with 30% acetone/hexane to give 25,25-ethylene-dioxy-27-norcholest-5-en-1α,3β-diol. (0.0125 g, Rf 0.22): NMR (270 MHz) δ0.68 (s, 18—$CH_3$), 0.93 (d, J=6.9 Hz, 21—$CH_3$), 1.03 (s, 19—$CH_3$), 1.31 (s, 26—$CH_3$), 3.85 (m, 1β—H), 3.93 (ethylene ketal), 3.97 (septet, J=5.4 Hz, 3α—H), 5.58 (m, 6—H).

A solution of this product (12.5 mg, 0.028 mmol) and a catalytic amount of p-toluenesulfonic acid in ethanol (2 ml) was stirred at room temperature for 5 hr. TLC (50% acetane/hexane developed three times) showed only one spot, Rf 0.55. The ethanol was removed and methylene chloride was added. The organic phase was washed with dilute $NaHCO_3$ and water and evaporated to give 5 (R=hydrogen): NMR (270 MHz) δ0.68 (s, 18—$CH_3$), 0.94 (d, J=6.6 Hz, 21—$CH_3$), 1.04 (s, 19—$CH_3$), 2.13 (s, 26—$CH_3$), 3.85 (m, 1α—H), 3.98 (m, 3α—H), 5.60 (m, 6—H); mass spectrum m/e (relative intensity, calcd. mass) 402.3151 ($M^+$, 0.50, calcd for $C_{26}H_{42}O_3$, 402.3134), 387.2898 ($M^+$—$CH_3$, 0.07, 387.2899) 384.3042 ($M^+$—$H_2O$, 1.00, 384.3028), 366.2922 ($M^+$—2×$H_2O$, 0.18, 3.66.2922), 289.2169 ($M^+$—side chain, 0.13, 289.2167), 271.2061 ($M^+$—$H_2O$-side chain, 0.13, 271.2061), 253.1957 ($M^+$—2×$H_2O$-side chain, 0.13, 253.1957).

A solution of the diol product in pyridine (0.5 ml) and acetic anhydride (0.5 ml) was heated at 90° C. under $N_2$ for 2.5 hr. The reaction was quenched with cold water and $K_2CO_3$. The product was extracted with $Et_2O$. The organic phase was washed with 1 N HCl, dilute $NaHCO_3$, water and brine and dried ($Na_2SO_4$). Evaporation of the ether gave 12.4 mg of 5 (R=acetyl) which was homogenous on TLC (50% acetone/hexane, Rf 0.65).

EXAMPLE 5

1α,3β-Dihydroxy-27-nor-cholest-5,7-diene-25-one 1α,3β-Diacetate (6).

(R=acetyl). To 5 (R=acetyl) (12.4 mg, 0.025 mmol) and $NaHCO_3$ (14 mg) in hexane (0.5 ml) was added 1,3-dibromo-5,5-dimethylhydantoin (3.9 mg, 0.013 mmol). After heating for 20 min at 80° C. under $N_2$, the reaction mixture was cooled and filtered. The hexane was evaporated and the residue was dissolved in dry xylene (0.5 ml) and 2,4,6-trimethylpyridine (50 μl) and heated at reflux under $N_2$ for 90 min. The cooled reaction mixture was diluted with benzene and washed with 1 N HCl, dilute $NaHCO_3$, water and brine. The organic phase was evaporated to dryness and the residue obtained was dissolved in dioxane (0.5 ml) containing p-toluenesulfonic acid (1.5 mg) and heated at 70° under $N_2$ for 40 min. The material obtained after work-up was purified by TLC developed twice with 10% acetone/hexane to give the diene-diacetate 6 (R=acetyl) (2.9 mg, Rf 0.29): UV (EtOH) $\lambda_{max}$ 293, 281, 271, 262 nm; mass spectrum m/e (relative intensity) 484 ($M^+$, 0.01), 424 ($M^+$—AcOH, 0.08), 364 ($M^+$—2×AcOH, 1.00), 549 ($M^+$—2×AcOH—$CH_3$, 0.05), 251 ($M^+$—2×AcOH-side chain, 0.10), 118 (0.84).

EXAMPLE 6

1α-Hydroxy-27-nor-25-ketovitamin $D_3$ (7).

A solution of 6 (R-acetyl) in 20% EtOH/benzene (150 ml) under $N_2$ at 0° C. was irradiated for 20 min in a quartz reaction vessel with a 125 watt Hanovia 8A36 lamp fitted with a corex filter. The solvent was evaporated and the recovered 1α-hydroxy-25-keto-27-norprevitamin $D_3$ 1,3-diacetate was dissolved in heptane and heated under $N_2$ at 85° C. for 4 hr to yield 1α-hydroxy-25-keto-27-norprevitamin $D_3$ 1,3-diacetate. The solvent was removed and the residue dissolved in ether (0.5 ml) and 0.1 M KOH/MeOH (0.5 ml) and allowed to stand for 2.5 hr at room temperature. The solvent was removed and ether and water were added. The phases were separated and the organic phase was washed with water. The vitamin analog 7 was purified by high-pressure liquid chromatography (HPLC) 0.6×25 cm microparticulate silica gel column) developed with 6% 2-propanol/hexane. Compound 7 eluted from 151 to 158 ml. An analytical sample was homogeneous when re-injected into HPLC: UV (ethanol) $\lambda_{max}$ 265, $\lambda_{min}$ 228 nm, $\lambda_{max}/\lambda_{min}$ 1.7; mass spectrum m/e (relative intensity) 400.2973 ($M^+$, 0.10 calcd. for $C_{24}H_{40}O_3$, 400.2977), 382.2868 ($M^+$—$H_2O$, 0.51, 382.2872), 364.2798 ($M^+$—2×$H_2O$, 0.39, 364.2766), 269.1913 ($M^+$—$H_2O$-side chain, 0.06, 269.1905), 251.1792 ($M^+$—2×$H_2O$-side chain, 0.12, 215.1800), 152.0828 (0.36, $C_9H_{11}O_2$, 152.0837), 134.0735 (1.00, $CH_9H_{10}O$, 134.0732).

EXAMPLE 7

Preparation of 25-keto-27-norvitamin $D_3$ (compound 8).

To a solution of 25-keto-27-norcholesterol (2.0 g) in 5.0 ml of pyridine was added 1.0 ml acetic anhydride and the mixture was heated to 50° for 4 hr. The mixture was then poured into crushed ice, solid $K_2CO_3$ was added, and the aqueous mixture was extracted with ether. The ether phases were washed with 1 N HCl solution, dilute $NaHCO_3$ solution, then with water and brine, and dried over sodium sulfate. After evaporation of the ether solvent, the residue was chromatographed over silica gel (4.5×4 cm column) eluted with 600 ml of 30% ethyl acetate in hexane, to yield 1.8 g of the 3-acetate product (compound 1, where R=acetyl). To 250 mg of 25-keto-27-norcholesterol 3-acetate (1), R=acetyl) dissolved in 8.5 ml of hexane and 5.5 ml of benzene was added solid $NaHCO_3$ (285 mg) and 115 mg of 1,3-dibromo-5,5-dimethylhydantoin. After heating the mixture at 80° C. under $N_2$ for 20 min., it was filtered and the residue was rinsed well with dry benzene. The total filtrate solution was evaporated and the residue was taken up in 8.5 ml of dry xylene to which 2.0 ml of s-collidine was added. This mixture was refluxed under $N_2$ for 1.5 hr, then cooled, diluted with water and extracted with ether. The ether extracts were washed (1 N HCl, dilute $NaHCO_3$, $H_2O$ and brine) and dried ($Na_2SO_4$), then filtered and the solvent evaporated.

The residue was dissolved in 8 ml of dioxane, 35 mg of p-toluene sulfonic acid was then added, and the mixture was heated at 70° for 30 min. Water was added and the product was extracted with ether. The ether phases were washed (dil. $NaHCO_3$, $H_2O$ and brine) dried over $Na_2SO_4$, filtered and solvent evaporated).

To the residue, in 5 ml of ether, 3 ml of 5% KOH in methanol were added and the mixture was stirred at room temperature for 1 hr. After addition of water, the mixture was extracted with ether, the extracts were washed ($H_2O$ and brine) dried ($Na_2SO_4$) and solvent was evaporated. The residue after chromatography on silica gel plates (0.75 mm thick), developed with 25% ethyl acetate in chloroform gave 88 mg of the desired product, 25-keto-27-nor-7-dehydrocholesterol. This 5,7-diene product dissolved in ether (150 ml) was irradiated under $N_2$ for 5 min at 0° using a Hanau lamp with Vycor filter. Solvent was then evaporated and the residue was chromatographed on silica gel thin layer plates developed twice with 25% ethylacetate/$CHCl_3$, to yield the previtamin product (25-keto-27-norprevitamin $D_3$).

This product, dissolved in 2 ml of $CCl_4$ was heated at 80° for 3.5 hr under $N_2$, to effect isomerization. Evaporation of solvent gave 25-keto-27-nor-vitamin $D_3$ (compound 8).

EXAMPLE 8

6-methoxy-25-keto-27-nor-3,5-cyclovitamin $D_3$ (compound 9, Z=Me).

A solution of 20 mg of 25-ketovitamin 8 in 0.25 ml of dry pyridine was treated with 40 mg of toluenesulfonyl chloride. After 90 hr at 5°, ice chips and 10% $NaHCO_3$ solution were added, and the mixture was extracted into ether. The ether phases were washed (1 N HCl, dil. $NaHCO_3$, water, brine) and dried over $MgSO_4$. After evaporation of solvent the 3-tosylated product (20 mg) was dissolved in 2 ml of dry methanol and 0.3 ml of dry benzene, 100 mg $NaHCO_3$ was added and the mixture was warmed to 55° for 20 hr. After addition of $H_2O$, the mixture was extracted with ether, ether extracts were washed ($H_2O$ and brine), dried ($MgSO_2$), and evaporated to yield 20 mg of the desired 3,5-cyclovitamin product 9 (Z=methyl).

EXAMPLE 9

1α-Hydroxy-6-methoxy-25-keto-27-nor-3,5-cyclovitamin $D_3$ (10, Z=Me).

To 1.9 mg of $SeO_2$ in 0.7 ml of dry $CH_2Cl_2$ at 0°, 10 μl of 90% t-butyl hydroxyperoxide was added and the mixture stirred for 30 min at 0°. To this mixture 20 mg of cyclovitamin product 9 (Z=Me) in 0.7 ml of $CH_2Cl_2$ was added dropwise, and the reaction was allowed to proceed for 12 min at room temperature. The reaction was quenched by addition of sat. $NaHCO_3$ solution and the mixture was extracted with $CH_2Cl_2$. The organic extracts were washed (dil. $NaHCO_3$, water, brine) dried ($MgSO_4$) and the product was purified by thin-layer chromatography. (silica gel, 40% ethylacetate/hexane). In this way, 5 mg of 1α-hydroxycyclovitamin product 10 (Z=methyl) was obtained, which was characterized by its mass spectrum and proton nmr spectrum.

Treatment of compound 10 (1 mg) with acetic anhydride (0.1 ml) in pyridine (0.1 ml) at 55° for 1.5 hr yielded the corresponding 1α-acetoxy derivative. Similarly the 1α-benzoate is prepared by reaction of 10 with benzoyl chloride (in pyridine at room temperature for 3 hrs.)

EXAMPLE 10

1α-Hydroxy-25-keto-27-norvitamin $D_3$ (Compound 7).

The 1α-hydroxy-6-methoxy-25-keto-27-nor-3,5-cyclovitamin $D_3$ product (10 mg) was taken up in 0.5 ml of glacial acetic acid and heated at 55° for 15 min. Crushed ice and enough $NaHCO_3$ to neutralize the reaction mixture was then added and the mixture was extracted with ether. The ether extracts were washed (dil. $NaHCO_3$, $H_2O$, brine) dried ($MgSO_4$) and evaporated. The residue containing chiefly the desired 1α-hydroxy-25-keto-27-norvitamin $D_3$ 3-acetate product (compound 11, R=acetyl) and the corresponding 5,6-trans isomer was then chromatographed (high pressure liquid chromatography, using a 0.62×25 cm column of Zorbax-SIL and 2.5% 2-propanol in hexane as eluting solvent; Zorbax-SIL is a microparticulate silica gel preparation, a product of Dupont and Co., Wilmington, Del.). The desired cis-vitamin product 11 (R=acetyl) eluted at 103 ml and after recycling once was obtained in pure form (3.4 mg) and characterized by its proton nmr spectrum. The corresponding 5,6-trans isomer, 1α-hydroxy-25-keto-5,6-trans-27-norvitamin $D_3$ 3-acetate eluted at 112 ml and was recovered in pure form.

The 3-acetate product 11 (R=acetyl), thus obtained was hydrolyzed in a solution of ether (0.5 ml) and 0.1 M KOH/MeOH (0.1 ml). Hydrolysis was complete after 1 hr at room temperature, after which water was added, and the mixture was extracted with ether. Extracts were washed with water and brine, dried over $MgSO_4$ and solvent was evaporated to yield 2.9 mg of 1α-hydroxy-25-keto-27-norvitamin $D_3$, (compound 7), exhibiting ultraviolet, nuclear magnetic resonance and mass spectra exactly in accord with the structure and in accord with the data obtained for the same product documented in Example 6 above.

Identical hydrolysis of the 3-acetate derivative of the 5,6-trans product yielded 1α-hydroxy-25-keto-5,6-trans-27-norvitamin $D_3$ (UV: $\lambda_{max}$ 273 nm; mass spectrum m/e 400 (M+), 152, 134).

BIOLOGICAL ACTIVITY

Weanling male rats (Holtzman Co., Madison, Wis.) were housed in hanging wire cages and fed ad libitum a low calcium, vitamin D-deficient diet as described by Suda et al (J. Nutr. 100, 1049 (1970)) for 2–3 weeks prior to their use in the following assays.

INTESTINAL CALCIUM TRANSPORT

Rats were divided into six groups of six animals and each was administered a single dose of the test compounds dissolved in 0.05 ml of 95% ethanol by intrajugular injections. Amounts administered are given in the table below. Group 1, the control group received only the solvent vehicle (0.05 ml 95% ethanol). Twenty-four hours after compound injection the rats were killed by decapitation and their duodena were used to measure calcium transport activity according to the techniques of Martin and DeLuca (Am. J. Physiol. 216, 1351 (1969)). Results are shown in the table below.

| Group | Compound Given | $^{45}Ca$ serosal/$^{45}Ca$ mucosal (mean ± SEM) |
|---|---|---|
| 1 | EtOH | 2.1 ± 0.2 |
| 2 | 12.5 ng 1,25-$(OH)_2D_3$[a] | 4.6 ± 0.2 |
| 3 | 0.5 μg compound 7[b] | 2.3 ± 0.2 |
| 4 | 2.5 μg compound 7 | 3.2 ± 0.3 |
| 5 | 12.5 μg compound 7 | 3.2 ± 0.4 |
| 6 | 25 μg compound 7 | 3.7 ± 0.3 |

[a]1,25-$(OH)_2D_3$ = 1α,25-dihydroxyvitamin $D_3$
[b]compound 7 = 1α-hydroxy-25-keto-27-norvitamin $D_3$

BONE CALCIUM MOBILIZATION (Elevation of serum calcium concentration).

Rats fed as above were divided into groups of six animals each, which were given 0.05 ml of 95% ethanol (the control groups) or various amounts of the test compounds (as indicated in the table below) dissolved in 0.05 ml of 95% ethanol by intrajugular injection. The materials were administered as single doses, 6 or 24 hr before sacrifice. The rats were killed by decapitation after the indicated times, their blood was collected and centrifuged to obtain serum. An aliquot of the serum (0.1 ml) was mixed with 1.9 ml of a 0.1% lanthanum chloride solution and the calcium concentration in serum (an indication of the liberation of bone calcium in response to test compound) was measured with an atomic absorption spectrophotometer (Perkin Elmer Model HO-214). Results are shown in the table below.

| Compound Given | Serum $Ca^{++}$ (mg/100 ml) 6 hr mean + SEM | 24 hr mean + SEM |
|---|---|---|
| EtOH (control) | 4.2 ± 0.1 | 3.7 ± 0.2 |
| 12.5 ng 1,25-$(OH)_2D_3$[a] | 4.5 ± 0.2 | 4.7 ± 0.2 |
| 0.500 μg compound 7[b] | 4.5 ± 0.1 | 3.6 + 0.1 |
| 2.5 μg compound 7 | 5.2 ± 0.1 | 3.9 ± 0.2 |
| 12.5 μg compound 7 | 5.3 ± 0.2 | 4.3 ± 0.2 |
| 25 μg compound 7 | 5.2 ± 0.1 | 4.4 ± 0.3 |

[a]1,25-$(OH)_2D_3$ = 1α,25-dihydroxyvitamin D
[b]compound 7 = 1α-hydroxy-25-keto-27-norvitamin $D_3$ It is evident from the foregoing data that 1α-hydroxy-25-keto-27-norvitamin $D_3$ (compound 7) exhibits pronounced vitamin D like activity. Particularly noteworthy in this regard is the rapid onset of activity (see 6 hr time points in the table above), which compares with that of 1,25—$(OH)_2D_3$, the most rapidly acting vitamin $D_3$ derivative known heretofore.

Aside from its utility as a biologically active analog of vitamin $D_3$, the compound of this invention is also useful as a synthetic intermediate for the preparation of other desirable vitamin D compounds. For example, treatment of this 1α-hydroxy-25-ketovitamin compound with a methyl Grignard reagent (e.g. $CH_3MgBr$ or $CH_3MgI$) or a methyl lithium reagent, yields 1α,25-dihydroxyvitamin $D_3$, the most potent metabolite of vitamin $D_3$ known. The 25-keto derivative thus can serve as the starting material for a simple and straightforward preparation of this highly desirable metabolite. Even more importantly the 25-ketone derivative can serve as starting material for the synthesis of 1,25—$(OH)_2D_3$ in highly radioactive form. Thus treatment of the ketone with tritiated methyl Grignard or methyl lithium reagent provides directly (26,27—$^3H$)-1,25—$(OH)_2D_3$ and with appropriate $^{14}C$-labeled reagents the same reaction provides (26,27—$^{14}$C)-1,25—(OH)$_2$D$_3$. By this method, radiolabeled 1,25-(OH)$_2$D$_3$ of extremely high specific activity can be prepared in a single, easily conducted reaction step (e.g. (26,27—$^3$H)-1,25—(OH)$_2$D$_3$ with specific activity of 80 Ci/mmole can be prepared). Analogously, trideutero- or $^{13}$C-labeled 1,25—(OH)$_2$D$_3$ is readily prepared by treatment of ketone (7) with the appropriate isotopically labeled Grignard or alkyl lithium reagents which are readily prepared by well-known methods from the commercially available isotopically labeled methyl halides (e.g. C$^2$H$_3$I, $^{13}$CH$_3$I, etc.)

Since 5,6-trans vitamin D$_3$ compounds can be isomerized by irradiation with ultraviolet light to the corresponding 5,6-cis isomers, as is well-known in the art, the 5,6-trans-1α-hydroxy-25-keto-27-norvitamin D$_3$ product obtained by the processes of this invention has utility by virtue of its photochemical conversion to the 5,6-cis product.

In the claims, the term "lower alkyl" signifies an alkyl group of from 1 to about 4 carbons such as methyl, ethyl, isobutyl, sec. butyl, t-butyl and the term "acyl" implies an acyl group such as formyl, acetyl, benzoyl or nitrobenzoyl.

We claim:

1. 1α-hydroxy-25-keto-27-nor-vitamin D$_3$ and acylates thereof.

2. 1α-hydroxy-25-keto-27-nor-previtamin D$_3$ and acylates thereof.

3. 1α,3β-dihydroxy-27-nor-cholesta-5,7-dien-25-one and acylates thereof.

4. 1α,3β-dihydroxy-27-nor-cholest-5-en-25-one and acylates thereof.

5. Compounds of the structure

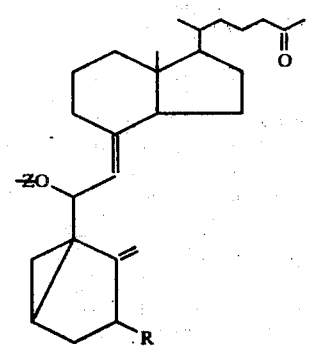

where R is selected from hydrogen, hydroxy and O-acyl and where Z is selected from hydrogen or lower alkyl.

6. The compound of claim 5 where R is hydrogen and Z is methyl.

7. The compound of claim 5 where R is hydroxy and Z is methyl and the acylates thereof.

8. 1α-hydroxy-25-keto-5,6-trans-27-norvitamin D$_3$ and acylates thereof.

* * * * *